(12) United States Patent
Gellman et al.

(10) Patent No.: US 7,879,054 B2
(45) Date of Patent: Feb. 1, 2011

(54) SYSTEM AND METHOD FOR TISSUE SAMPLING AND THERAPEUTIC TREATMENT

(75) Inventors: Barry N. Gellman, N. Easton, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1278 days.

(21) Appl. No.: 10/798,085

(22) Filed: Mar. 11, 2004

(65) Prior Publication Data
US 2005/0203440 A1 Sep. 15, 2005

(51) Int. Cl.
*A61B 17/32* (2006.01)
(52) U.S. Cl. ...................................... 606/167; 600/567
(58) Field of Classification Search .................. 606/167, 606/170; 600/562, 567
See application file for complete search history.

(56) References Cited
U.S. PATENT DOCUMENTS

| | | | | |
|---|---|---|---|---|
| 5,607,389 A | * | 3/1997 | Edwards et al. | 604/22 |
| 5,788,651 A | * | 8/1998 | Weilandt | 600/567 |
| 6,213,957 B1 | * | 4/2001 | Milliman et al. | 600/566 |
| 6,306,132 B1 | * | 10/2001 | Moorman et al. | 606/41 |
| 6,497,706 B1 | * | 12/2002 | Burbank et al. | 606/45 |
| 6,692,490 B1 | * | 2/2004 | Edwards | 606/41 |
| 2001/0014779 A1 | * | 8/2001 | Burbank et al. | 600/564 |

* cited by examiner

*Primary Examiner*—Gary Jackson
*Assistant Examiner*—Victor X Nguyen
(74) *Attorney, Agent, or Firm*—Finnegan, Henderson, Farabow, Garrett & Dunner LLP

(57) ABSTRACT

A biopsy system comprises a first placeholder element insertable through tissue to a first selected location in a patient's body, the first placeholder element including a first element guide and a tissue sampling element insertable to the first selected location via the first element guide for obtaining a sample of tissue from the first selected location, the tissue sampling element being removable from the first element guide while leaving the first placeholder element at the first selected location in combination with a tissue treatment element insertable to the first selected location via the first element guide.

21 Claims, 5 Drawing Sheets

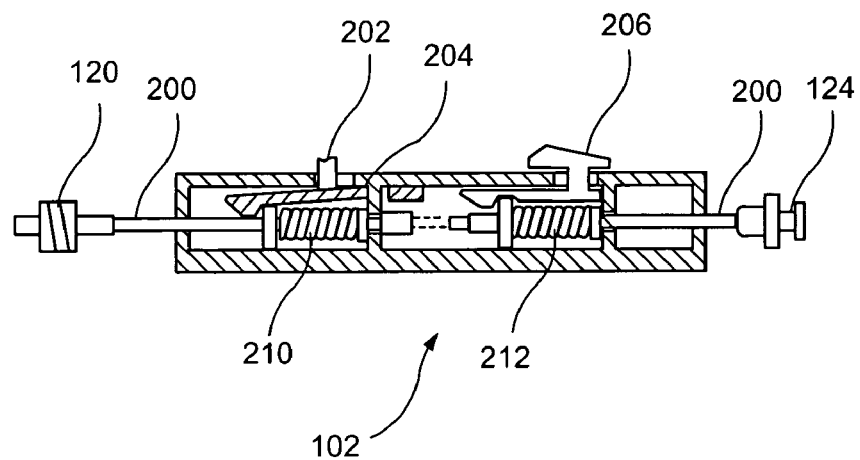
F I G. 2
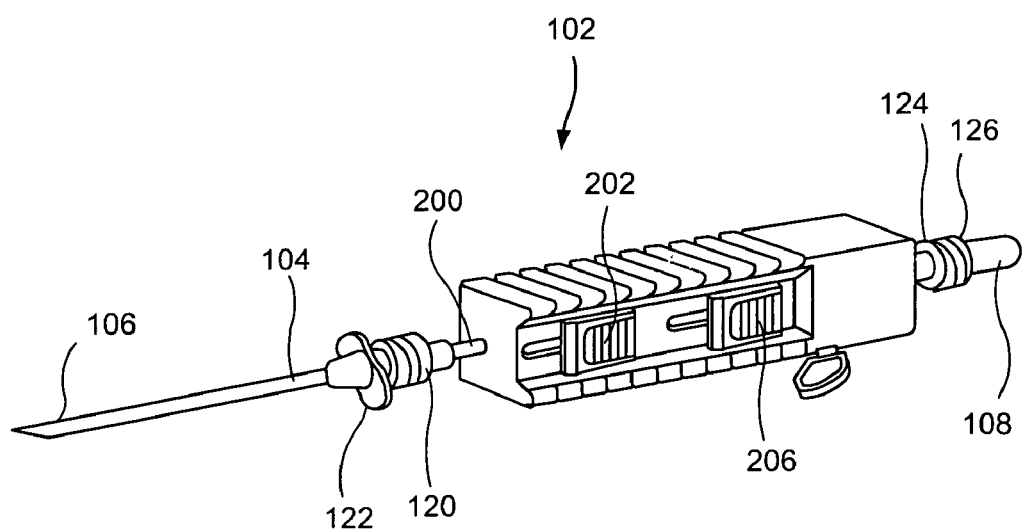
F I G. 3

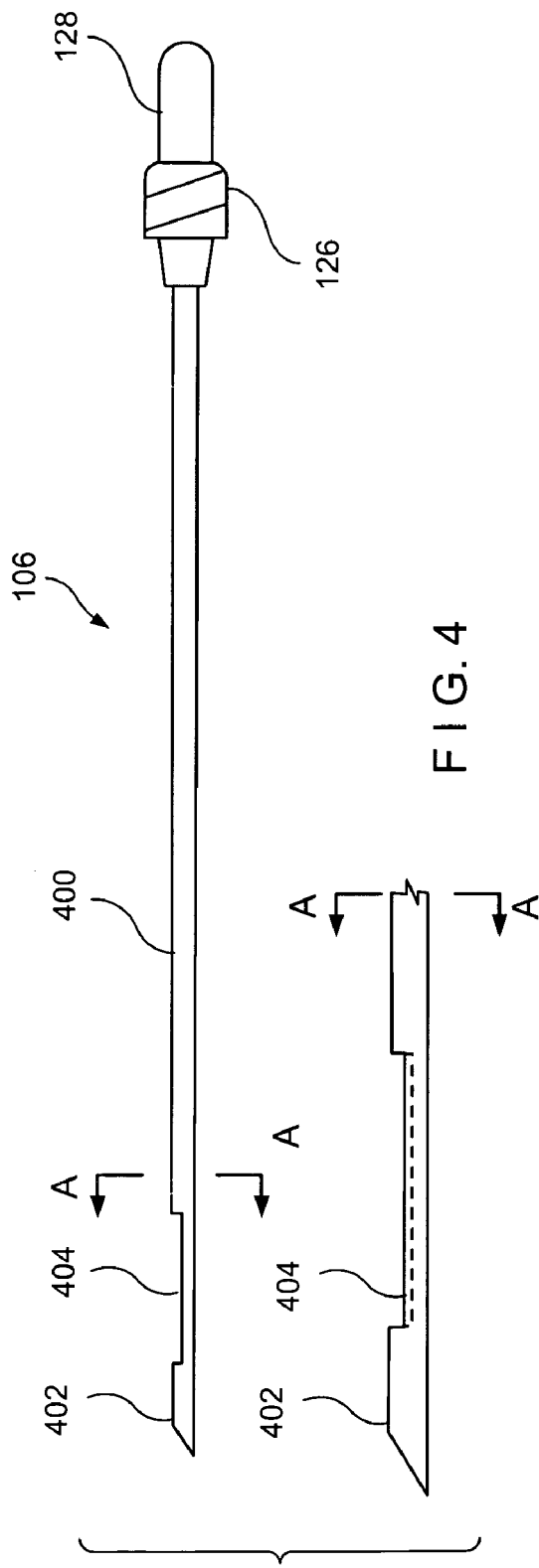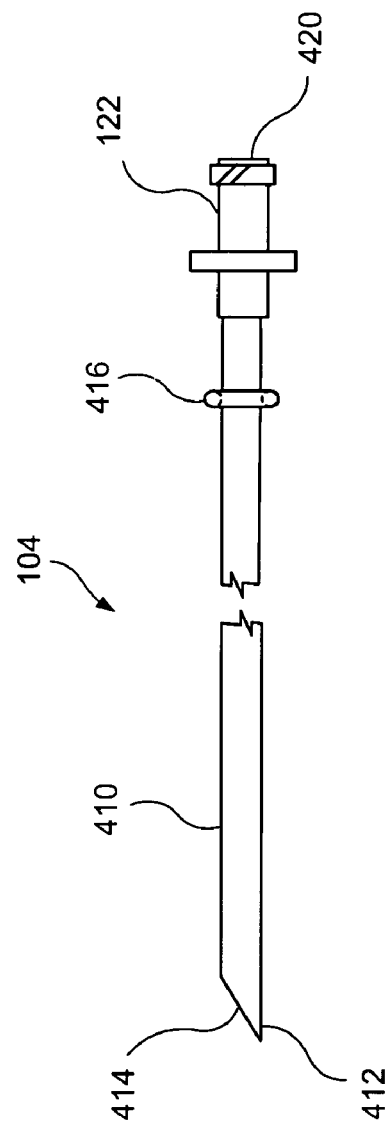

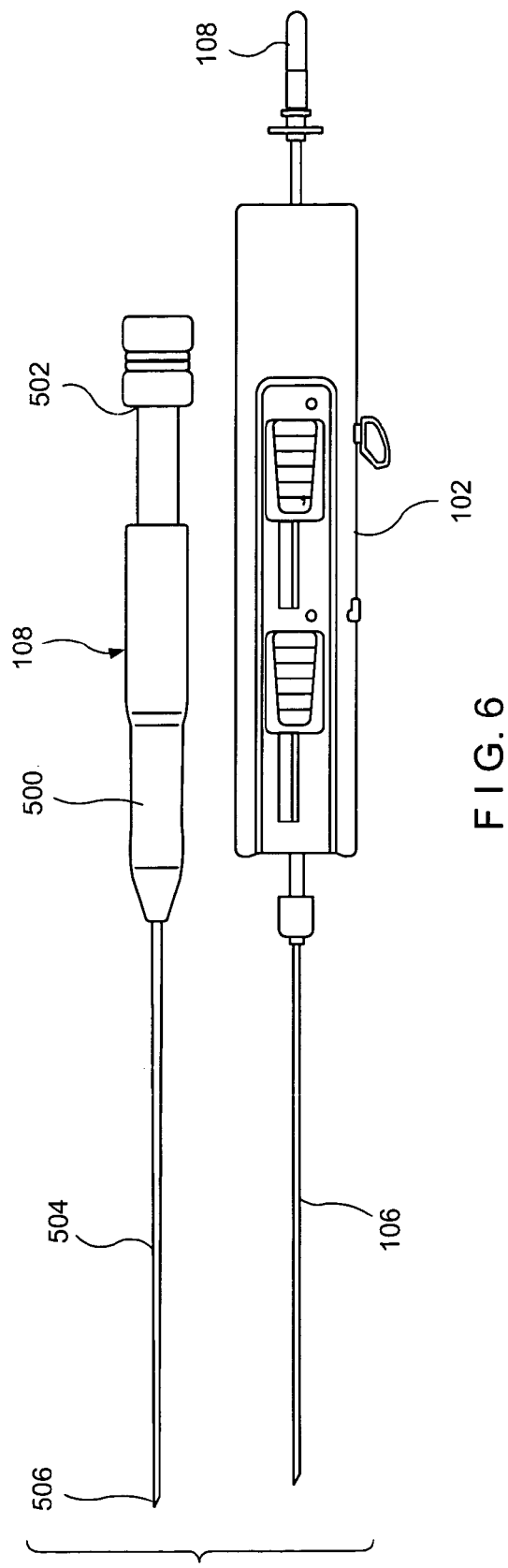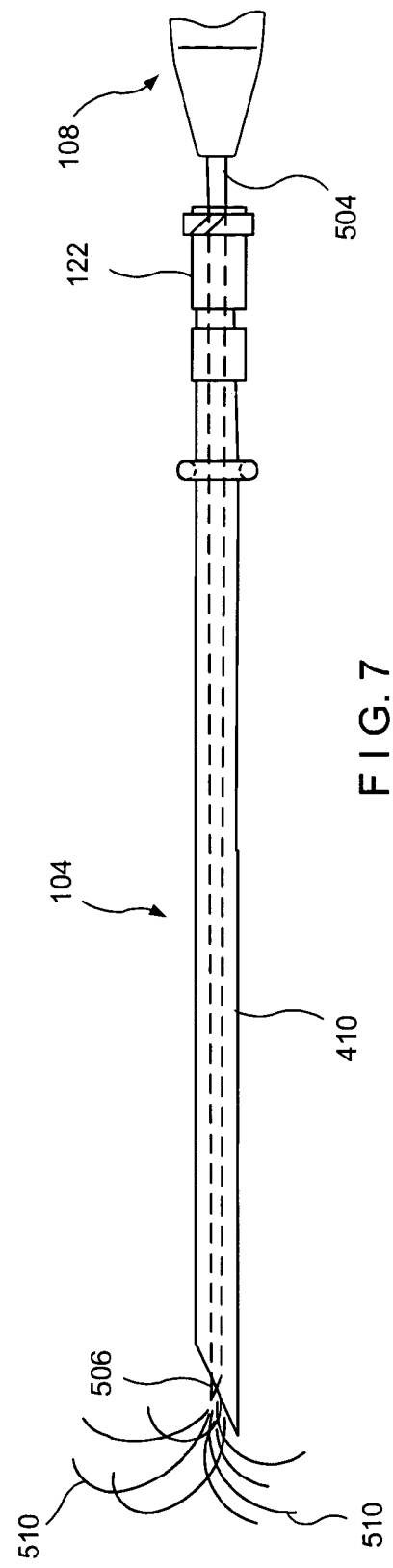
FIG. 6
FIG. 7

SYSTEM AND METHOD FOR TISSUE SAMPLING AND THERAPEUTIC TREATMENT

BACKGROUND

The diagnosis and treatment of tissues that are suspected of being cancerous typically requires the patient to undergo several procedures. In many cases, a needle biopsy is carried out. This procedure involves inserting a hollow needle into the suspect tissue and withdrawing a sample via the hollow core of the needle. The biopsy sample is then sent to a pathology laboratory and analyzed to determine whether it contains cancer cells, or whether some other abnormal condition exists.

This type of biopsy is very useful in evaluating localized abnormalities and is especially beneficial, for example, in the diagnosis of cancers of the liver, prostate and kidney. Surgical biopsies generally involve the creation of larger wounds and, consequently, larger areas of scarring. As a result, needle biopsies are often preferred since patient discomfort, scarring and recovery time are reduced with respect to surgical biopsies.

During a needle biopsy, access to the suspect tissue is somewhat limited by the size of the needle and, as a result, it is often difficult or impossible to carry out additional procedures during the biopsy. Accordingly, tissue characterization procedures and therapeutic interventions are usually carried out separately from the biopsy, at a later time. After the biopsy, it may take some time to receive results of the tissue analysis from the pathology laboratory and this may further delay the beginning of treatment. If the sample is found to be insufficient or unsuitable for analysis, another biopsy must be performed, which requires re-introducing the biopsy needle at the selected location to remove another sample.

Depending on the diagnosis, therapy may be required to remove or treat the diseased tissue. In many cases, the tissue may be removed using any of a variety of minimally invasive methods. For example, a variety of treatments such as lumpectomy or ablation techniques may be available. Electrical currents may be applied to treat the tissues, or a chemical treatment substance may be employed for the same purpose. The treatment methods described herein are generally used to cause the destruction of targeted tissue through substances harmful to the targeted tissue. These substances include, for example, salts, long & short term acting pellets, radiation sources (e.g., high dose, through a placeholder, low dose in the form of brachytherapy seeds) etc. References to ablation or to other specific methods for the treatment of diseased tissue are for illustrative purposes only and are not intended to limit the application of the system and method according to the invention.

In general, these treatment procedures are carried out after the diagnostic steps have been performed, since it often takes time to evaluate tissue samples. To reach the tissue, the tissue treatment devices are positioned in the same area targeted by the biopsy. Positioning these devices takes time with the surgeon repeating several steps that were already taken while performing the biopsy.

In many cases, treatment may require repeated therapeutic sessions in which a needle or other device must be re-inserted into the same portion of tissue. This causes discomfort to the patient and also increases the time and cost of the operation. Scarring due to repeated insertion of a needle may also make it progressively more difficult to correctly place the therapeutic device within the diseased tissue, so that efficacy of the treatment may be reduced. Likewise, in cases where it is necessary to take additional biopsy samples from the affected site, the same steps described above are repeated, with the ensuing patient discomfort and extended time for the procedure.

SUMMARY OF THE INVENTION

In one aspect the present invention is directed to a biopsy system comprising a first placeholder element insertable through tissue to a first selected location in a patient's body, the first placeholder elements including a first element guide and a tissue sampling element insertable to the first selected location via the first element guide for obtaining a sample of tissue from the first selected location, the tissue sampling element being removable from the first element guide while leaving the first placeholder element at the first selected location in combination with a tissue treatment element insertable to the first selected location via the first element guide.

In a different aspect, the present invention is directed to a method for treating tissue, comprising the steps of inserting a placeholder element into a body to a selected tissue location and inserting to the selected location a tissue sampling element through a lumen of the placeholder element in combination with the steps of operating the tissue sampling element via a handle connected to the placeholder element, detaching the handle from the placeholder element and directing a tissue treatment element to the selected location via the placeholder element. Then the tissue treatment element is operated to treat the tissue at the selected location.

BRIEF DESCRIPTION OF DRAWINGS

FIG. 2 is a cross sectional view of a handle element of a medical diagnostic and treatment device according to an embodiment of the present invention;

FIG. 3 is a perspective view of the handle element shown in FIG. 2;

FIG. 4 is a side elevation view of a tissue sampling element according to an embodiment of the present invention;

FIG. 5 is a side elevation view of a place holder element according to an embodiment of the present invention;

FIG. 6 is a diagram showing a handle element connected to a tissue sampling element and a tissue treatment element according to an embodiment of the present invention;

FIG. 7 is a diagram showing a deployed distal end of the tissue treatment element shown in FIG. 6.

DETAILED DESCRIPTION

Figure 1:
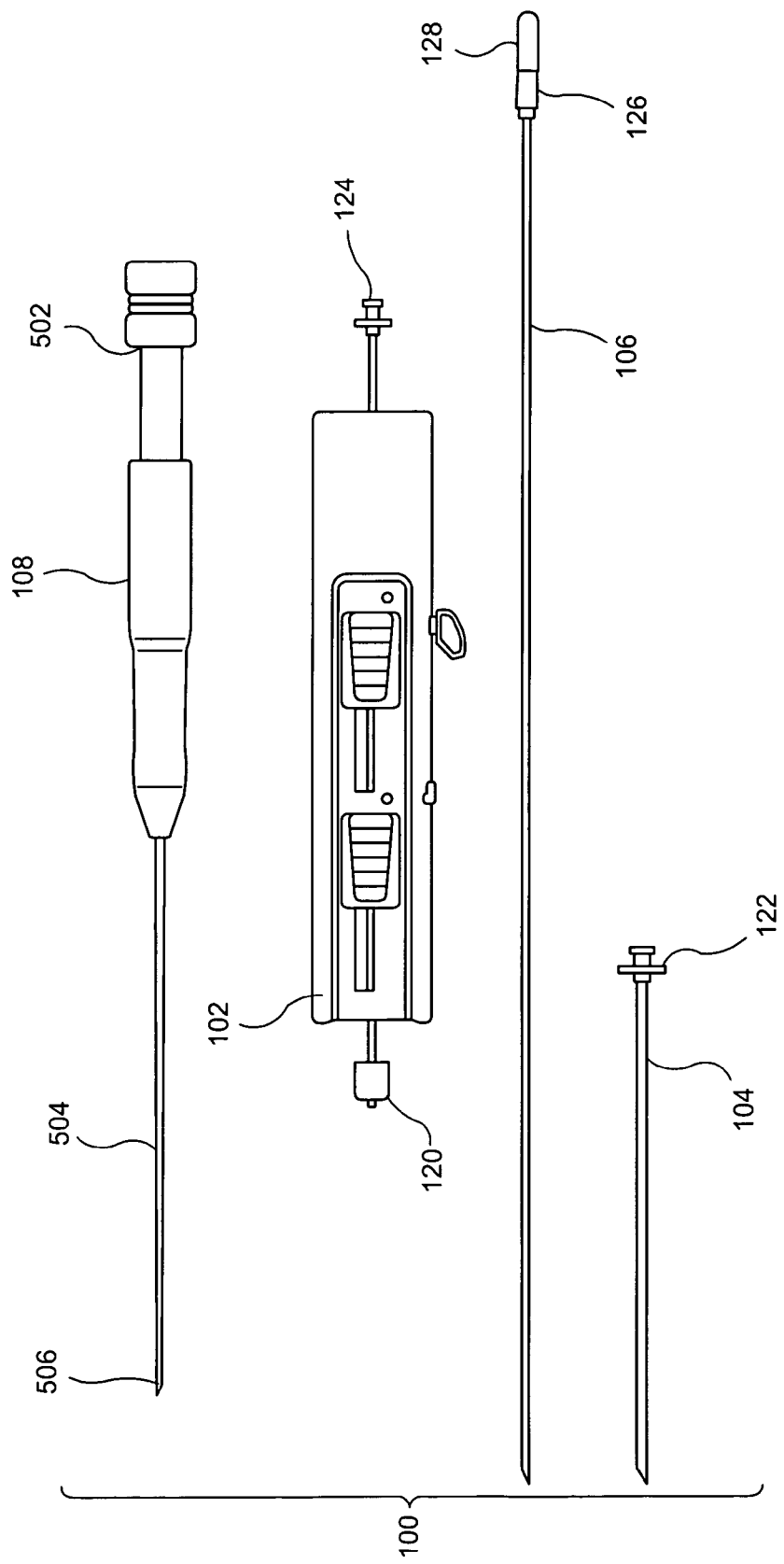
FIG. 1 is a diagram showing an embodiment of a tissue sampling and therapeutic system according to the present invention.

The present invention may be further understood with reference to the following description and the appended drawings, wherein like elements are referred to with the same reference numerals. The present invention is related to medical devices that are used to sample, diagnose and treat localized diseases of tissue within a patient. In particular, the present invention relates to biopsy devices having the capability of carrying out diagnostic and therapeutic tasks on the tissue object of the biopsy.

Various embodiments of the present invention improve on current methods of diagnosis and treatment for localized tissue diseases, and permit the surgeon to sample, diagnose and treat the tissue at the same time, using the same system. More specifically, embodiments of the present invention provide a device, a system and a method to carry out diagnosis and therapy of localized tissue through, for example, lumpectomy or ablation. The embodiments may comprise, for example, diagnostic elements to sample tissues for the presence of cancer or to evaluate tissue morphology. Also included are placeholder elements that remain in position within the tissue while the diagnosis takes place, to mark the selected location in the tissue so it is easily accessible by therapeutic elements designed to deliver appropriate therapy to the tissue.

An exemplary embodiment of the system for sampling, diagnosis and treatment of localized tissue is shown in FIG. 1. Here, the system 100 comprises a handle element 102, a placeholder element 104, and a tissue sampling element 106. In addition, the system may include a tissue treatment element 108. These components will be described in greater detail below. This system is optimized to perform a needle biopsy and includes a removable placeholder element 104 which in this case comprises a needle with a conduit formed therein which can be connected to the handle element 102 via luer fittings 120, 122. The tissue sampling element 106 which may be inserted through the handle element 102 and through the placeholder element 104, in this example comprises a removable biopsy cutting needle connectable to the handle element 102 via the luer fittings 124, 126.

The handle element 102 is connectable to several accessory elements of the system. FIGS. 2 and 3 show the handle element 102 in greater detail, including a quick release connection to the placeholder element 104 via, for example, the luer 120, 122 at the distal end of the handle element 102. The handle element 102 also includes conduits 200 that extend from the proximal and distal ends of the body of the handle. The conduits 200 form part of an accessory element channel extending through the handle portion 102, and are adapted to receive the tissue sampling element 106 therethrough. As will be explained below, the conduits 200 need not be continuous through the handle element 102, and instead may have openings that expose the tissue sampling element 106 to control and actuation components. A luer 124 may be used in conjunction with the luer 126 to form a quick-release connection between the handle element 102 and the tissue sampling element 106.

Various devices to control the operation of the system 100 may be included within the handle element 102. In particular, controls to operate the tissue sampling element 106 may be included within the handle element 102 so that the surgeon may easily and positively command various operations of the tissue sampling element 106. In the embodiment shown in the drawings, the handle portion 102 comprises a cutting actuation safety 202 which, when engaged, prevents actuation of the a cutting device of the tissue sampling element 106. By actuating the safety 202, the surgeon moves the needle lock 204 to a locking position preventing inadvertent cutting by the tissue sampling element 106. Once the tissue sampling element 106 has been positioned at a selected location within the tissue, the needle lock 204 may be released by moving the safety 202 to enable the removal of a sample via the tissue sampling element 106.

A needle cutter actuator 206 may be provided in the handle element 102 to activate a cutting device of the tissue sampling element 106 so that, when the surgeon operates the actuator 206, a sample is cut from the suspect tissue. As shown, resilient elements may be used to bias the controls toward desired default positions. For example, a spring 210 may be used to bias the cutting actuation safety 202 to the "locked" position. Similarly, another spring 212 may be used to bias the cutter actuator 206 toward the non-cutting position. Those of skill in the art will understand that the specific details of both the cutter actuator 206 and the cutting actuation safety 202 may be conventional, and may be selected to suit the specific operating environment of the handle element 102.

A more detailed view of the tissue sampling element 106 according to the exemplary embodiment of the invention is shown in FIG. 4, which includes a detailed view A-A of a distal tip region thereof. The tissue sampling element 106 comprises a needle body 400 designed to reach the selected location within the suspect tissue. The needle 400 may be adapted to pass through the conduits 200 of the handle element 102, so that the surgeon can grasp the latter to accurately manipulate the needle 400. A sharp tip 402 may be included at the distal end thereof to facilitate penetration of the patient's tissues en route to the selected location. In addition, a cutting portion 404 may be formed near the tip 402, to perform the resection necessary to obtain a tissue sample. The specific design of the cutting portion 404 may be selected depending on the type and location of the tissue being sampled. For example, for certain situations it may be desirable to include a cutting portion 404 which is actuated by rotating the needle 400 around a longitudinal axis thereof. Alternatively, the cutting portion 404 may be shrouded until released for operation by the surgeon. The tissue sample may be removed together with the needle 400 after cutting by, for example, pulling the needle out of the tissue using grasping portion 128.

In an exemplary use, the tissue sampling element 106 is connected to the handle portion 102 as described above and as shown in FIG. 6, and is inserted into the patient's tissue. Actuation of the cutting portion 404 severs a tissue sample which may be retrieved by detaching the needle 400 from the handle portion 102 and removing the sample with the needle 400. Alternatively, tissue sampling may be accomplished by suction biopsy, where the cutting portion 404 of the needle 400 gathers the tissue sample and suction is applied to draw the tissue sample to a collection means for withdrawal from the body. In some cases, tissue characterization may be performed in-vivo as the biopsy is ongoing. For example, an optical biopsy, photonic molecular probing, an X-ray phase contrast medical micro imaging method, an ultrasound system for disease detection, an ultrasound tissue assessment or other rapid detection method may be employed. Using any of the above mentioned methods may result in a diagnosis of the diseased tissue contemporaneously with the biopsy.

FIG. 5 shows an embodiment of a placeholder element according to the invention. The placeholder element 104 is placed in the tissue at the selected location for retention therein until an assessment or diagnosis of the tissue's condition has been completed and treatment is begun. In the exemplary embodiment, the placeholder element 104 comprises a placeholder needle 410 that is releasably attached to the handle element 102. Since the placeholder needle 410 is detachable from the handle element 102, sampling at multiple sites may be carried out by simply attaching to the handle element 102 a placeholder needle 410, placing the placeholder needle 410 at a first selected location, performing the procedure and detaching the handle element 102 from the placeholder needle 410 which is left in place in the tissue. The process may then be repeated at a second selected location (In the treatment of prostate cancer, 6-12 locations may be needed) with a second placeholder needle 410. In this manner, the surgeon may return to the various selected locations marked by the placeholder needles 410 at a later time, to perform further diagnostics or to treat the various areas.

The exemplary placeholder needle 410 has an internal lumen or conduit 414 extending there through which is sufficiently wide to accommodate the tissue sampling element 106. In this manner, the handle element 102 may be connected to the placeholder needle 410 so that the tissue sampling element 106 can follow the conduit 200 and the lumen 414 to the selected location in the tissue. After the tissue sampling element 106 has been withdrawn, the handle element 102 may be disconnected from the placeholder needle 410, which remains in position within the tissue. Therapeutic devices such as the tissue treatment element 108 may then be inserted through the lumen 414 to reach the selected location in the tissue and carry out additional procedures. The placeholder needle 410 may include a sharp distal end 412 adapted to pierce tissue and to anchor itself in the tissue after the selected location has been reached.

In one embodiment, means to identify the various placeholder needles 410 used in the course of a procedure may be provided. For example, each placeholder needle 410 may include a color coded or numbered tag 420 to more easily relate the various biopsy samples obtained in a procedure to the locations at which tissue treatment or other treatments may be needed. Each of the placeholder needles 410 may also include a friction ring 416 to provide a visual reference of movement of the corresponding placeholder needle 410. The friction ring 416 may be slidable along a diameter of the placeholder needle 410 and may be pushed against the patient's skin by the surgeon to mark the original depth of insertion.

Figure 8:
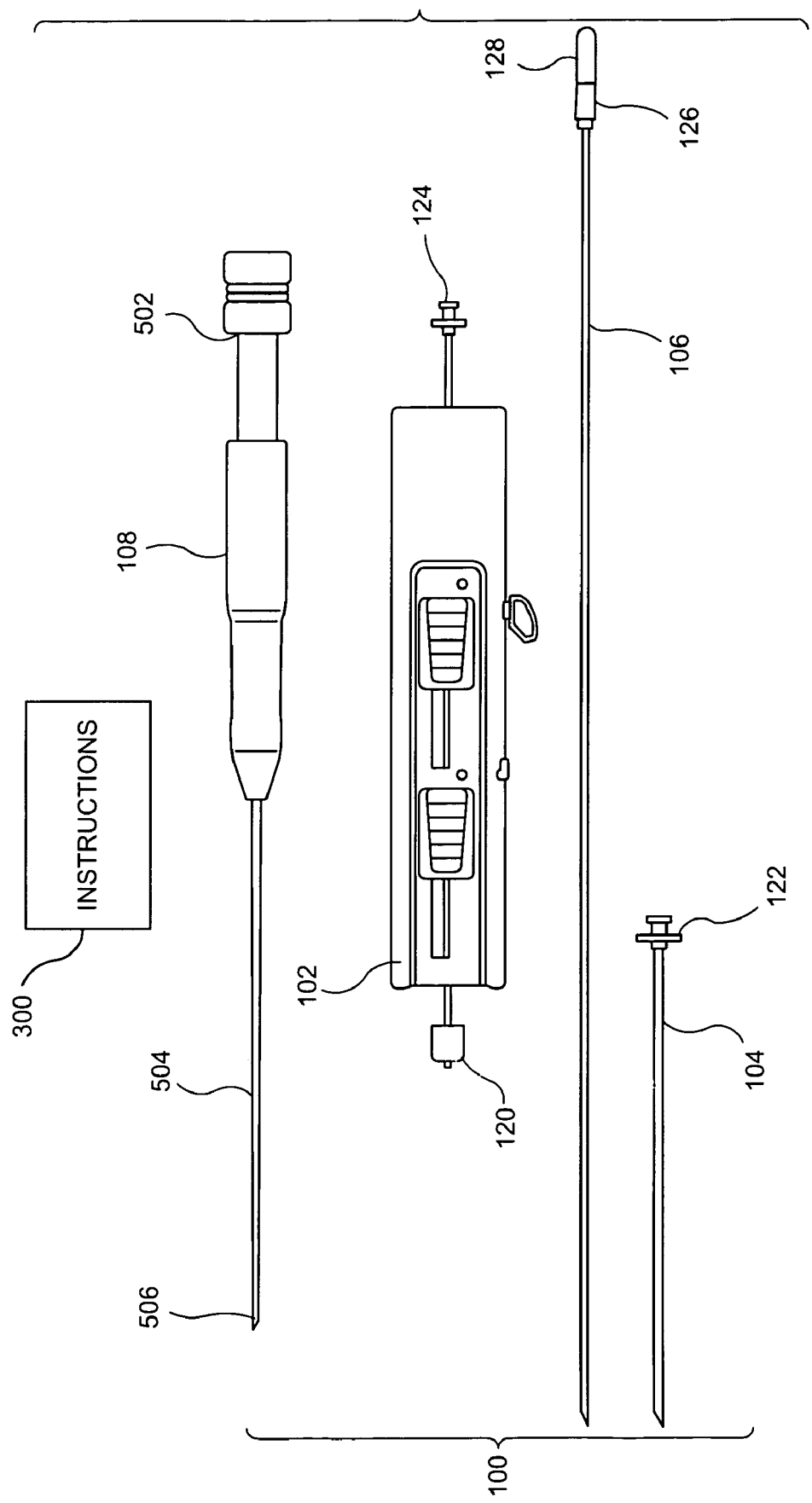
FIG. 8 shows a kit including the system of claim 1 along with instructions for performing the method for treating tissue described herein.

Once the diagnostic part of the procedure has been completed, the placeholder element 104 functions as an access port for therapeutic devices that may be utilized to treat the selected tissue. For example, a tissue treatment device 108 as shown in FIGS. 1, 8 may be employed to progressively remove diseased tissue. In the exemplary embodiment, the tissue treatment device 108 is a radio frequency (RF) device which operates by delivering electrical energy to the selected site to cause necrosis of the surrounding tissue. Electrical RF devices may be monopolar or bipolar, with the bipolar devices being generally more effective in causing tissue necrosis. However, the bipolar devices generally employ a more complex delivery system as they require two separate electrodes located near one another. The embodiments of the present invention may be devised to provide either monopolar or bipolar electrodes, depending on the procedure's requirements.

FIG. 7 shows an exemplary multi-barbed electrode deployable through the lumen 414 of the placeholder element 104. The deployment of the treatment device 108 may be performed manually, for example, with a surgeon advancing a handle 500 thereof distally using a control portion 502. In this example, barbed electrodes 510 form a pattern of electrodes extending from a distal tip portion 506 of a tubular extension 504 of the treatment element 108 which is insertable through the placeholder element 104. The tubular extension 504 may be inserted through the lumen 414 and pushed therethrough to reach the selected portion of the patient's tissue. The electrodes 510 are then energized to initiate treatment. In one exemplary embodiment, the barbed electrodes 510 form a plurality of different poles with the polarity thereof alternating between neighboring electrodes. In another exemplary embodiment, the placeholder needle 410 may form a first pole of the system, with barbed electrodes 510 providing a plurality of second poles.

Additional embodiments of the present invention may be devised which utilize other methods for treatment of the targeted tissue. For example. Instead of RF energy, the targeted tissue may be treated using laser energy, high pressure water jets, or the delivery of a radiation dose. The latter therapy may include delivery of a low dose using brachytherapy, or delivery of a more short term but stronger dose.

In another exemplary embodiment, the tissue treatment element 108 is not designed to deliver electrical energy to the affected tissue. Instead, a chemical tissue treatment substance may be delivered through placeholder element 104. For example, a liquid, a gel, a solid or a semi-solid containing alcohol or salt may be injected into the selected tissue through the place holder element 104 to cause disruption and necrosis of the selected tissue. Pain killer compounds, antiseptics or other therapeutic substances may also be introduced, alone or in addition to the above mentioned substances. In those exemplary embodiments in which the placeholder needle 410 is not used as an electrical pole, it may preferably be formed of non-conductive material or electrically insulated from radio frequency current to prevent interference with any electrically conductive poles employed by the system.

Many elements of the system 100 described above will preferably be formed of biocompatible materials as would be understood by those skilled in the art. For example, stainless steel may be used for the needle portions of the placeholder element 104 and the tissue sampling element 106. Polymeric materials may be used for the various handles and other elements which not subject to excessive loads. It will be apparent to those of skill in the art that different materials and different arrangements of the described parts may be devised, without departing from the scope of the present invention.

Exemplary steps that may be used by a surgeon to diagnose and treat cancer or other tissue conditions using the present invention are described below. The procedure may be initiated by attaching a placeholder element 104 to the handle element 102 and then inserting the assembly into the patient until the distal end of the placeholder element 104 reaches the selected location in the suspect tissue. The tissue sampling element 106 is then threaded through the conduit 200 of the handle element 102, and through the lumen of the placeholder element 104, until its distal tip 402 reaches the selected location. Using the controls on the handle element 102, the surgeon severs a tissue sample and retrieves it, for example, while withdrawing the tissue sampling element 106 from the body. At this point the handle element 102 may be detached and removed, leaving the placeholder element 104 in the tissue, providing a path to the selected location.

The same procedure may then be repeated at other locations, leaving additional placeholder elements 104 in the body to mark the additional locations. If necessary, tissue samples may be retrieved from any or all of the selected locations by re-inserting the tissue sampling element 106 in the various placeholder elements 104. After the diagnostic procedures have been completed, a tissue treatment element 108 may be used to treat any or all of those locations (e.g., any locations where cancer or other diseased tissue was found). Depending on the diagnostic procedures used, it may take minutes or days before tissue removal is performed. However, as would be understood by those skilled in the art, optical means and/or biosensors may be utilized to diagnose cancer nearly immediately. In these cases, therapy could be initiated more quickly. In any case, the placeholder elements 104 may be left in place until the procedures have been completed. For example, when indicated by the diagnosis, an RF energy tissue treatment element 108 may be inserted into one or more of the placeholder elements 104 to necrose the corresponding tissue. After the tissue ablation treatment has been completed, the tissue treatment element 108 may be withdrawn from the placeholder element 104 and the placeholder 104 may be removed from the tissue or left in place for further treatments.

FIG. 8 shows a kit including the system 100 of FIG. 1 along with a booklet 300 providing step-by-step instructions for performing the method of diagnosing and treating adverse tissue conditions described above.

The present invention has been described with reference to specific exemplary embodiments. Those skilled in the art will understand that changes may be made in details, particularly in matters of shape, size, material and arrangement of parts. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed is:

1. A biopsy system comprising:
   a first placeholder element insertable through tissue to a first selected location in a patient's body, the first placeholder element including a first lumen extending therethrough to a distal opening which, when the first placeholder element is in the first selected location is adjacent to target tissue;
   a handle including a channel extending therethrough for directing elements inserted thereinto to the first lumen, the handle further including a handle fitting projecting distally from a distally facing surface of the handle configured to be received by a correspondingly shaped placeholder fitting in a proximal end of the first placeholder element and to be removed from the placeholder fitting when the handle fitting and the placeholder fitting are twisted relative to each other so that the first placeholder element may be left in the first selected location;
   a tissue sampling element insertable to the first selected location via the first lumen for obtaining a sample of tissue from the first selected location, the tissue sampling element being removable from the first lumen while leaving the first placeholder element at the first selected location; and
   a tissue treatment element insertable to the first selected location via the first lumen.

2. The system according to claim 1, wherein the handle includes a sampling element actuator for operating the tissue sampling element when the tissue sampling element has been inserted therethrough to the first lumen.

3. The system according to claim 2, wherein the handle further comprises a sampling safety lock which, when in a locked configuration, prevents actuation of the sampling element actuator.

4. The system according to claim 1, further comprising a second placeholder element insertable through tissue to a second selected location in a patient's body the second placeholder element including a second lumen extending therethrough, the second placeholder element removably receivable in the channel.

5. The system according to claim 4, wherein the first and second placeholder elements comprise identification markings.

6. The system according to claim 4, further comprising a first luer attachment for coupling the first placeholder element to the channel.

7. The system according to claim 6, wherein the tissue sampling element comprises a second luer attachment for coupling the tissue sampling element to the channel.

8. The system according to claim 1, wherein the tissue sampling element comprises a biopsy needle.

9. The system according to claim 8, wherein the biopsy needle includes a suction lumen for applying suction to a sample of tissue for removal of the sample from the body.

10. The system according to claim 1, wherein the tissue sampling element further comprises an in-vivo tissue treatment device.

11. The system according to claim 1, wherein the tissue treatment element is insertable through the first lumen of the first placeholder element when the first placeholder element is separate from the handle.

12. The system according to claim 1, wherein the tissue treatment element comprises one of a monopolar and a bipolar electrode.

13. The system according to claim 1, wherein the tissue treatment element comprises a conduit for insertion of a chemical treatment substance to the first selected location.

14. The system according to claim 1, wherein the tissue treatment element is coupleable to a source of electric power and employs the first placeholder element as an electrode.

15. The system according to claim 1, wherein the handle fitting is a male luer connector and the placeholder fitting is a female luer connector.

16. A biopsy system comprising:
   a first placeholder element insertable through tissue to a first selected location in a patient's body, the first placeholder element including a first element guide;
   a handle including a channel extending therethrough for directing elements inserted thereinto to the first element guide, the handle including a handle fitting projecting distally from a distally facing surface of the handle configured to be received by and removed from a proximal end of the first placeholder element;
   a tissue sampling element insertable to the first selected location through the first element guide for obtaining a sample of tissue from the first selected location, the tissue sampling element being removable from the first element guide while leaving the first placeholder element at the first selected location; and
   a tissue treatment element insertable to the first selected location through the first element guide, the tissue treatment element being insertable through the first element guide when the first placeholder element has been separated from the handle, wherein the tissue treatment element includes an electrode, and wherein the electrode is a multi-barbed electrode.

17. The system according to claim 16, wherein the tissue treatment element is removably insertable into a proximal end of the placeholder element.

18. A biopsy system comprising:
   a first placeholder element insertable through tissue to a first selected location in a patient's body, the first placeholder element including a first lumen extending therethrough to a distal opening, which, when the first placeholder element is in the first selected location, is adjacent to target tissue;
   a handle including a channel extending therethrough for directing elements inserted into a proximal opening of the handle to the first lumen of the first placeholder element, the handle including a handle fitting projecting distally from a distally facing surface of the handle configured to be received by a correspondingly shaped placeholder fitting on a proximal end of the first placeholder element and to be removed from the placeholder fitting when the handle fitting and the placeholder fitting are twisted relative to each other so that the first placeholder element may be left in the first selected location;

a tissue sampling element insertable through the proximal opening of the handle and the first lumen for obtaining a sample of tissue from the first selected location, the tissue sampling element being removable from the proximal opening of the handle while leaving the first placeholder element at the first selected location; and a tissue treatment element insertable to the first selected location through the first lumen.

19. The system according to claim 18, wherein the handle includes a second fitting extending proximally from a proximally facing surface of the handle configured to releasably engage a connector on the tissue sampling element.

20. The system according to claim 18, wherein the handle fitting is a male luer connector and the placeholder fitting is a female luer connector.

21. The system according to claim 18, wherein the tissue treatment element is removably insertable through a proximal end of the placeholder element.

* * * * *